United States Patent
Küçüksen et al.

(10) Patent No.: US 10,729,706 B2
(45) Date of Patent: Aug. 4, 2020

(54) PSILOCYBIN AND/OR PSILOCIN IN COMBINATION WITH CANNABINOIDS AND/OR TERPENES

(71) Applicant: Procare Beheer B.V., Hazerswoude-Dorp (NL)

(72) Inventors: Murat Küçüksen, Hazerswoude-Dorp (NL); Ali Neset Küçüksen, Hazerswoude-Dorp (NL)

(73) Assignee: Procare Beheer B.V., Hazerswoude-Dorp (NL)

( * ) Notice: Subject to any disclaimer, the term of this patent is extended or adjusted under 35 U.S.C. 154(b) by 0 days.

(21) Appl. No.: 16/478,283

(22) PCT Filed: Jan. 18, 2018

(86) PCT No.: PCT/NL2018/050037
§ 371 (c)(1),
(2) Date: Jul. 16, 2019

(87) PCT Pub. No.: WO2018/135943
PCT Pub. Date: Jul. 26, 2018

(65) Prior Publication Data
US 2019/0350949 A1    Nov. 21, 2019

(30) Foreign Application Priority Data

Jan. 18, 2017  (NL) ..................................... 2018190

(51) Int. Cl.
*A61K 31/675*  (2006.01)
*A61K 31/04*  (2006.01)
*A61K 31/015*  (2006.01)
*A61K 31/355*  (2006.01)
*A61P 25/28*  (2006.01)
*A61P 25/22*  (2006.01)
*A61P 25/18*  (2006.01)
*A61P 25/24*  (2006.01)
*A61K 31/352*  (2006.01)
*A61K 31/4045*  (2006.01)

(52) U.S. Cl.
CPC .......... *A61K 31/675* (2013.01); *A61K 31/352* (2013.01); *A61K 31/4045* (2013.01); *A61P 25/18* (2018.01); *A61P 25/22* (2018.01); *A61P 25/24* (2018.01); *A61P 25/28* (2018.01)

(58) Field of Classification Search
CPC .... A61K 31/675; A61K 31/04; A61K 31/015; A61K 31/335
USPC ................................... 514/80, 454, 762, 764
See application file for complete search history.

(56) References Cited

FOREIGN PATENT DOCUMENTS

| GB | 2383721 A | 4/2004 |
|---|---|---|
| GB | 2438682 A | 12/2007 |
| WO | WO 2009/043395 A2 | 4/2009 |
| WO | WO 2016/187277 A1 | 11/2016 |

*Primary Examiner* — Raymond J Henley, III
(74) *Attorney, Agent, or Firm* — Hoffmann & Baron, LLP

(57) ABSTRACT

One or more cannabinoids and/or terpenes in combination with psilocybin and/or psilocin may be used in the prevention or treatment of psychological or brain disorders. The one or more cannabinoids may be taken from the group of cannabidiol (CBD); cannabidiolic acid (CBDA); tetrahydrocannbidivarin (THCV); tetrahydrocannbidivarinin acid (THCVA); cannabichromene (CBC); cannabichromenic acid (CBCA); cannabigerol (CBG) and cannabigerolic acid (CBGA).

19 Claims, No Drawings

PSILOCYBIN AND/OR PSILOCIN IN COMBINATION WITH CANNABINOIDS AND/OR TERPENES

CROSS-REFERENCE TO RELATED APPLICATIONS

This application is the National Stage of International Application No. PCT/NL2018/050037, filed Jan. 18, 2018, which claims the benefit of Netherlands Application No. 2018190, filed Jan. 18, 2017, the contents of which is incorporated by reference herein.

TECHNICAL FIELD

The present disclosure provides for psilocybin and/or psilocin in combination with at least one cannabinoid and/or at least terpene for use in the prevention or treatment of psychological and brain disorders, wherein the at least one cannabinoid and/or the at least one terpene is administered separately, sequentially or simultaneously to the psilocybin and/or psilocin

BACKGROUND

Depression is a state of low mood and aversion to activity or apathy that can affect a person's thoughts, behaviour, feelings and sense of well-being.

People with a depressed mood can feel sad, anxious, empty, hopeless, helpless, worthless, guilty, irritable, angry, ashamed or restless. They may lose interest in activities that were once pleasurable, experience loss of appetite or overeating, have problems concentrating, remembering details or making decisions, experience relationship difficulties and may contemplate, attempt or commit suicide. Insomnia, excessive sleeping, fatigue, aches, pains, digestive problems or reduced energy may also be present.

Depressed mood is a feature of some psychiatric syndromes such as major depressive disorder, but it may also be a normal reaction, as long as it does not persist long term, to life events such as bereavement, a symptom of some bodily ailments or a side effect of some drugs and medical treatments. A DSM diagnosis distinguishes an episode (or 'state') of depression from the habitual (or 'trait') depressive symptoms someone can experience as part of their personality.

A number of psychiatric syndromes feature depressed mood as a main symptom. The mood disorders are a group of disorders considered to be primary disturbances of mood. These include major depressive disorder (MDD; commonly called major depression or clinical depression) where a person has at least two weeks of depressed mood or a loss of interest or pleasure in nearly all activities; and dysthymia, a state of chronic depressed mood, the symptoms of which do not meet the severity of a major depressive episode. Another mood disorder, bipolar disorder, features one or more episodes of abnormally elevated mood, cognition and energy levels, but may also involve one or more episodes of depression. When the course of depressive episodes follows a seasonal pattern, the disorder (major depressive disorder, bipolar disorder, etc.) may be described as a seasonal affective disorder. Outside the mood disorders: borderline personality disorder often features an extremely intense depressive mood; adjustment disorder with depressed mood is a mood disturbance appearing as a psychological response to an identifiable event or stressor, in which the resulting emotional or behavioral symptoms are significant but do not meet the criteria for a major depressive episode; and post-traumatic stress disorder, an anxiety disorder that sometimes follows trauma, is commonly accompanied by depressed mood. Depression is sometimes associated with substance use disorder. Both legal and illegal drugs can cause substance use disorder.

Questionnaires and checklists such as the Beck Depression Inventory or the Children's Depression Inventory can be used by a mental health provider to help detect, and assess the severity of depression. Semi structured interviews such as the Kiddie Schedule for Affective Disorders and Schizophrenia (KSADS) and the Structured Clinical Interview for DSM-IV (SCID) are used for diagnostic confirmation of depression.

Schizophrenia is a mental disorder characterized by abnormal social behaviour and failure to understand what is real. Common symptoms include false beliefs, unclear or confused thinking, hearing voices that others do not, reduced social engagement and emotional expression, and a lack of motivation. People with schizophrenia often have additional mental health problems such as anxiety disorders, major depressive illness, or substance use disorders. Symptoms typically come on gradually, begin in young adulthood, and last a long time.

Schizophrenia is diagnosed based on criteria in either the American Psychiatric Association's fifth edition of the Diagnostic and Statistical Manual of Mental Disorders (DSM 5), or the World Health Organization's International Statistical Classification of Diseases and Related Health Problems (ICD-10). These criteria use the self-reported experiences of the person and reported abnormalities in behavior, followed by a clinical assessment by a mental health professional. Symptoms associated with schizophrenia occur along a continuum in the population and must reach a certain severity before a diagnosis is made.

Schizophreniform disorder (acute schizophrenic episode) is characterized by the presence of some of the symptoms of schizophrenia including: delusions, hallucinations, disorganised speech, disorganised or catatonic behaviour, and negative symptoms. The disorder—including its prodromal, active, and residual phases—lasts longer than 1 month but less than 6 months. Schizoaffective disorder symptoms can vary greatly from patient to patient. Many patients suffer with problems with mood, daily function or intrusive thoughts. Other symptoms can include elevated, inflated or depressed mood; irritability and poor temper control; changes in appetite, energy and sleep; hallucinations (particularly auditory hallucinations); delusions of reference; paranoia; deteriorating concern with hygiene and disorganised or illogical speech.

Schizoaffective disorder features cycles of severe symptoms followed by improvement. Bipolar I disorder (mania, manic disorder, manicdepressive psychosis) is characterised by mood swings that range from low (feelings of intense depression and despair) to high (feelings of elation, referred to as "mania") and can be mixed, for example a depressed mood may be combined with restlessness and overactivity. Often both depressive and manic episodes are experienced.

Bipolar II disorder is characterised by hypomanic episodes as well as at least one major depressive episode. Hypomanic episodes do not go to the extremes of mania (i.e. do not cause social or occupational impairment, and are without psychotic features). Bipolar II is much more difficult to diagnose, since the hypomanic episodes may simply appear as a period of successful high productivity and is reported less frequently than a distressing depression. Psychosis can occur in manic and major depressive episodes, but not in hypomania. For both disorders, there are a number of specifiers that indicate the presentation and course of the disorder, including "chronic", "rapid cycling", "catatonic" and "melancholic"

Major depressive disorder with psychotic feature (psychotic depression) is characterised in that a patient in addition to suffering from depressive symptoms also suffers from hallucinations or delusions. These patients often become paranoid and may believe that their thoughts are not their own or that others can 'hear' their thoughts.

Delusional disorders (paranoia) are a form of psychosis where the patient has long-lasting paranoid delusions which have no other physical or medical cause. These delusions may also be accompanied by auditory hallucinations.

Shared psychotic disorder (shared paranoia disorder) is a very rare condition in which people close to a mentally ill person share his or her false beliefs (delusions). As an example, a man with schizophrenia may falsely believe that his children are trying to murder him. His wife develops shared psychotic disorder and comes to believe it as well. This disorder usually occurs in long-term relationships and involves two people. However, it can also develop among members of a group, such as within families. It affects women more often than men.

Brief psychotic disorder (other and unspecified reactive psychosis) is characterised by patients who experience an acute psychotic episode lasting longer than one day but less than one month and that may or may not immediately follow an important life stress or a pregnancy (with postpartum onset). This illness usually comes as a surprise as there is no forewarning that the person is likely to break down, although this disorder is more common in people with a pre-existing personality disorder. Paranoid personality disorder is characterised by an exaggeration of the cognitive modules for sensitivity to rejection, resentfulness, distrust, as well as the inclination to distort experienced events. Neutral and friendly actions of others are often misinterpreted as being hostile or contemptuous. Unfounded suspicions regarding the sexual loyalty of partners and loyalty in general as well as the belief that one's rights are not being recognized is stubbornly and argumentatively insisted upon. Such individuals can possess an excessive self-assurance and a tendency toward an exaggerated self reference. Pathological jealousy, instinctive aggressive counter-attack, the need to control others, and the gathering of trivial or circumstantial "evidence" to support their jealous beliefs also features.

Schizoid personality disorder (SPD) is characterised by a lack of interest in social relationships, a tendency towards a solitary lifestyle, secretiveness, and emotional coldness. SPD is reasonably rare compared with other personality disorders, its prevalence is estimated at less than 1% of the general population. Schizotypal personality disorder, is characterized by a need for social isolation, odd behaviour and thinking, and often unconventional beliefs such as being convinced of having extra-sensory abilities.

Psychosis and psychotic disorders are commonly treated with a class of medication known as atypical antipsychotics.

Anxiety disorders are a group of mental disorders characterized by feelings of anxiety and fear. Anxiety is a worry about future events and fear is a reaction to current events. These feelings may cause physical symptoms, such as a fast heart rate and shakiness. There are a number of anxiety disorders: including generalized anxiety disorder, specific phobia, social anxiety disorder, separation anxiety disorder, agoraphobia, and panic disorder. The disorder differs by what results in the symptoms. People often have more than one anxiety disorder.

The diagnosis of anxiety disorders is difficult because there are no objective biomarkers, it is based on symptoms, which typically need to be present at least six months, be more than would be expected for the situation, and decrease functioning. Several generic anxiety questionnaires can be used to detect anxiety symptoms, such as the State-Trait Anxiety Inventory (STAI), the Generalized Anxiety Disorder 7 (GAD-7), the Beck Anxiety Inventory (BAI), the Zung Self-Rating Anxiety Scale, and the Taylor Manifest Anxiety Scale. Other questionnaires combine anxiety and depression measurement, such as the Hamilton Anxiety Rating Scale, the Hospital Anxiety and Depression Scale (HADS), the Patient Health Questionnaire (PHQ), and the Patient-Reported Outcomes Measurement Information System (PROMIS). Examples of specific anxiety questionnaires include the Liebowitz Social Anxiety Scale (LSAS), the Social Interaction Anxiety Scale (SIAS), the Social Phobia Inventory (SPIN), the Social Phobia Scale (SPS), and the Social Anxiety Questionnaire (SAQ-A30).

Agoraphobia is an anxiety disorder characterized by symptoms of anxiety in situations where the person perceives the environment to be unsafe with no easy way to get away. These situations can include open spaces, public transit, shopping malls, or simply being outside the home. Being in these situations may result in a panic attack. The symptoms occur nearly every time the situation is encountered and lasts for more than six months. Those affected will go to great lengths to avoid these situations. In severe cases people may become unable to leave their homes.

Most people who present to mental health specialists develop agoraphobia after the onset of panic disorder. Agoraphobia is best understood as an adverse behavioral outcome of repeated panic attacks and subsequent anxiety and preoccupation with these attacks that leads to an avoidance of situations where a panic attack could occur. Early treatment of panic disorder can often prevent agoraphobia. Agoraphobia is typically determined when symptoms are worse than panic disorder, but also do not meet the criteria for other anxiety disorders such as depression. In rare cases where agoraphobics do not meet the criteria used to diagnose panic disorder, the formal diagnosis of agoraphobia without history of panic disorder is used (primary agoraphobia).

Attention deficit hyperactivity disorder (ADHD) is a mental disorder of the neurodevelopmental type. It is characterized by problems paying attention, excessive activity, or difficulty controlling behavior which is not appropriate for a person's age. These symptoms begin by age six to twelve, are present for more than six months, and cause problems in at least two settings (such as school, home, or recreational activities). ADHD often persists into adulthood, with resultant impairments of social, academic and occupational functioning. In children, problems paying attention may result in poor school performance. Although it causes impairment, particularly in modern society, many children with ADHD have a good attention span for tasks they find interesting.

ADHD is diagnosed by an assessment of a person's childhood behavioral and mental development, including ruling out the effects of drugs, medications and other medical or psychiatric problems as explanations for the symptoms. It often takes into account feedback from parents and teachers with most diagnoses begun after a teacher raises concerns. It may be viewed as the extreme end of one or more continuous human traits found in all people. Whether someone responds to medications does not confirm or rule out the diagnosis. As imaging studies of the brain do not give consistent results between individuals, they are only used for research purposes and not diagnosis.

In North America, DSM-5 criteria are used for diagnosis, while European countries usually use the ICD-10. With the DSM-IV criteria a diagnosis of ADHD is 3-4 times more likely than with the ICD-10 criteria. It is classified as neurodevelopmental psychiatric disorder. Additionally, it is classified as a disruptive behavior disorder along with oppositional defiant disorder, conduct disorder, and antisocial personality disorder. A diagnosis does not imply a neurological disorder.

Premenstrual dysphoric disorder (PMDD) is a severe and disabling form of premenstrual syndrome affecting 3-8% of menstruating women. The disorder consists of a "cluster of affective, behavioral and somatic symptoms" that recur monthly during the luteal phase of the menstrual cycle. PMDD was added to the list of depressive disorders in the Diagnostic and Statistical Manual of Mental Disorders in 2013. Authoritative diagnostic criteria for PMDD are provided by a number of expert medical guides, notably the Diagnostic and Statistical Manual of Mental Disorders V (DSM-V). The Diagnostic and Statistical Manual of Mental Disorders, Fifth Edition (DSM-5), established seven criteria (A through G) for the diagnosis of PMDD.

Premenstrual syndrome (PMS) refers to physical and emotional symptoms that occur in the one to two weeks before a woman's period. Symptoms often vary between women and resolve around the start of bleeding. Common symptoms include acne, tender breasts, bloating, feeling tired, irritability, and mood changes. Often symptoms are present for around six days. A woman's pattern of symptoms may change over time. Symptoms do not occur during pregnancy or following menopause.

Huntington's disease (HD), also known as Huntington's chorea, is an inherited disorder that results in death of brain cells. The earliest symptoms are often subtle problems with mood or mental abilities. A general lack of coordination and an unsteady gait often follow. As the disease advances, uncoordinated, jerky body movements become more apparent. Physical abilities gradually worsen until coordinated movement becomes difficult and the person is unable to talk. Mental abilities generally decline into dementia. The specific symptoms vary somewhat between people. Symptoms usually begin between 30 and 50 years of age, but can start at any age. The disease may develop earlier in life in each successive generation. About 8% of cases start before the age of 20 years and typically present with symptoms more similar to Parkinson's disease. People with HD often underestimate the degree of their problems.

Medical diagnosis of the onset of HD can be made following the appearance of physical symptoms specific to the disease. Genetic testing can be used to confirm a physical diagnosis if there is no family history of HD. Even before the onset of symptoms, genetic testing can confirm if an individual or embryo carries an expanded copy of the trinucleotide repeat in the HTT gene that causes the disease. Genetic counseling is available to provide advice and guidance throughout the testing procedure, and on the implications of a confirmed diagnosis. These implications include the impact on an individual's psychology, career, family planning decisions, relatives and relationships. Despite the availability of pre-symptomatic testing, only 5% of those at risk of inheriting HD choose to do so.

Alzheimer's disease (AD), also known as just Alzheimer's, is a chronic neurodegenerative disease that usually starts slowly and gets worse over time. It is the cause of 60% to 70% of cases of dementia. The most common early symptom is difficulty in remembering recent events (short-term memory loss). As the disease advances, symptoms can include problems with language, disorientation (including easily getting lost), mood swings, loss of motivation, not managing self care, and behavioural issues. As a person's condition declines, they often withdraw from family and society. Gradually, bodily functions are lost, ultimately leading to death. Although the speed of progression can vary, the average life expectancy following diagnosis is three to nine years.

Alzheimer's disease is usually diagnosed based on the person's medical history, history from relatives, and behavioural observations. The presence of characteristic neurological and neuropsychological features and the absence of alternative conditions is supportive.

Parkinson's disease (PD) is a long-term degenerative disorder of the central nervous system that mainly affects the motor system. The symptoms generally come on slowly over time. Early in the disease, the most obvious are shaking, rigidity, slowness of movement, and difficulty with walking. Thinking and behavioral problems may also occur. Dementia becomes common in the advanced stages of the disease. Depression and anxiety are also common occurring in more than a third of people with PD. Other symptoms include sensory, sleep, and emotional problems. The main motor symptoms are collectively called "parkinsonism", or a "parkinsonian syndrome". A physician will diagnose Parkinson's disease from the medical history and a neurological examination.

An autoimmune disease is a condition arising from an abnormal immune response to a normal body part. There are at least 80 types of autoimmune diseases. Nearly any body part can be involved. Common symptoms include low grade fever and feeling tired. Often symptoms come and go.

There is a significant requirement for an effective treatment that is able to prevent or treat the above-discussed psychological and brain disorders without resulting in side-effects.

SUMMARY OF THE INVENTION

According to the first aspect of the present disclosure there is provided for psilocybin and/or psilocin in combination with at least one cannabinoid and/or at least one terpene for use in the prevention or treatment of any of the above-discussed psychological and brain disorders, wherein the at least one cannabinoid and/or the at least one terpene is administered separately, sequentially or simultaneously to the psilocybin and/or psilocin. Further, the at least one cannabinoid may be administered separately, sequentially or simultaneously to the at least one terpene.

Despite the strong prejudice against *cannabis* and psilocybin/psilocin, the applicant believes there is significant credible evidence supporting the use of certain cannabinoid based medicines in combination with psilocybin/psilocin.

DETAILED DESCRIPTION OF THE INVENTION

Psilocybin is a naturally occurring psychedelic compound produced by more than 200 species of mushrooms, collectively known as psilocybin mushrooms. The most potent are members of the genus *Psilocybe*, such as *P. azurescens, P.*

*semilanceata*, and *P. cyanescens*, but psilocybin has also been isolated from about a dozen other genera.

Once ingested, psilocybin is rapidly metabolized to psilocin, which then acts on serotonin receptors in the brain. The mind-altering effects of psilocybin typically last from two to six hours, although to individuals under the influence of psilocybin, the effects may seem to last much longer, since the drug can distort the perception of time. Psilocybin has a low toxicity and a relatively low harm potential, and reports of lethal doses of the drug are rare. Several modern bioanalytical methods have been adapted to rapidly and accurately screen the levels of psilocybin in mushroom samples and body fluids. Since the 1990s, there has been a renewal of scientific research into the potential medical and psychological therapeutic benefits of psilocybin for treating conditions including obsessive-compulsive disorder (OCD), cluster headaches, and anxiety related to terminal cancer.

Psilocybin is also referred to as [3-(2-dimethylaminoethyl)-1H-indol-4-yl] dihydrogen phosphate, and given the CAS number 520-52-5.

Psilocin (also known as 4-HO-DMT, psilocine, psilocyn, or psilotsin) is a substituted tryptamine alkaloid and a serotonergic psychedelic substance. It is present in most psychedelic mushrooms together with its phosphorylated counterpart psilocybin.

Psilocin also referred to as 4-hydroxy-N,N-dimethyltryptamine, and given the CAS number 520-53-6.

Cannabinoids are a group of chemicals known to activate cannabinoid receptors in cells. These chemicals, which are found in *cannabis* plants, are also produced endogenously in humans and other animals. These are termed endocannabinoids. Synthetic cannabinoids are chemicals with similar structures to plant' cannabinoid or endocannabinoids and it is, of course, possible to also make synthetic versions of these plant cannabinoids or endocannabinoids.

Cannabinoids possess the characteristics of being cyclic molecules exhibiting particular properties such as the ability to easily cross the blood-brain barrier, weak toxicity and few side effects.

Plant cannabinoids or phyto-cannabinoids can also be isolated such that they are "essentially pure" compounds. These isolated cannabinoids are essentially free of the other naturally occurring compounds, such as, other minor cannabinoids and molecules such as terpenes.

Essentially pure compounds have a degree of purity up to at least 95% by total weight. Some essentially pure cannabinoids (whether synthetic or isolated) have been suggested to be neuroprotective agents, either by direct antagonism of the NMDA receptor or by reducing the influx of calcium ions into the cell by another means such as binding with cannabinoid receptors.

Preferably the one or more cannabinoids are taken from the group: cannabidiol (CBD); cannabidiolic acid (CBDA); tetrahydrocannbidivarin (THCV); tetrahydrocannbidivarinin acid (THCVA); cannabichromene (CBC); cannabichromenic acid (CBCA); cannabigerol (CBG) and cannabigerolic acid (CBGA).

Preferably the plurality of phyto-cannabinoids are present in the form of a *cannabis* plant extract, which depending on the composition of the extract, may have all or a proportion of THC or THCA selectively removed.

More preferably the cannabinoid extract from at least one *cannabis* plant is a botanical drug substance.

Preferably the cannabinoid extract from at least one *cannabis* plant is produced by extraction with supercritical or subcritical $CO_2$. Alternatively the cannabinoid extract from at least one *cannabis* plant is produced by contacting plant material with a heated gas at a temperature which is greater than 100° C., sufficient to volatilise one or more of the cannabinoids in the plant material to form a vapour, and condensing the vapour to form an extract. Alternatively the one or more cannabinoids, including phyto-cannabinoids, may be present in a substantially pure or isolated form.

A "substantially pure" preparation of cannabinoid is defined as a preparation having a chromatographic purity (of the desired cannabinoid) of greater than 90%, more preferably greater than 95%, more preferably greater than 96%, more preferably greater than 97%, more preferably greater than 98%, more preferably greater than 99% and most preferably greater than 99.5%, as determined by area normalisation of an HPLC profile.

Preferably the substantially pure cannabinoid used in the invention is substantially free of any other naturally occurring or synthetic cannabinoids, including cannabinoids that occur naturally in *cannabis* plants. In this context "substantially free" can be taken to mean that no cannabinoids other than the target cannabinoid are detectable by HPLC.

Substantially pure cannabinoids can be prepared from a botanical drug substance. A technique has been established by the applicant and is described in GB2393721.

In another aspect of the present invention the cannabinoid is in a synthetic form. References to cannabinoids, particularly with regard to therapeutic use, will be understood to also encompass pharmaceutically acceptable salts of the cannabinoid. The term "pharmaceutically acceptable salts" refers to salts or esters prepared from pharmaceutically acceptable non-toxic bases or acids, including inorganic bases or acids and organic bases or acids, as would be well known to persons skilled in the art. Many suitable inorganic and organic bases are known in the art.

The scope of the disclosure also extends to derivatives of cannabinoids that retain the desired activity. Derivatives that retain substantially the same activity as the starting material, or more preferably exhibit improved activity, may be produced according to standard principles of medicinal chemistry, which are well known in the art. Such derivatives may exhibit a lesser degree of activity than the starting material, so long as they retain sufficient activity to be therapeutically effective. Derivatives may exhibit improvements in other properties that are desirable in pharmaceutically active agents such as, for example, improved solubility, reduced toxicity, enhanced uptake, etc. Preferably, the cannabinoid combined with the psilocybin/psilocin is formulated as a pharmaceutical composition further comprising one or more pharmaceutically acceptable carriers, excipients or diluents.

The role of the at least one terpene in the present disclosure lies in its synergy with cannabinoids. Terpenes can correct or enhance the effect of the cannabinoids, so that in many cases, (much) less active components are needed to attain the desired effects. In the case of THC, terpenes can correct for the psychoactive effect (the "high"), which makes it much easier for the patient to maintain all normal daily activities.

Terpenes (or terpenoids) are volatile organic compounds that are found in every plant and are rather prevalent in *cannabis*. Terpenes are what make each *cannabis* strain its unique smell and taste. Terpenes work synergistically with cannabinoids and contribute to the medical benefits of the *cannabis* plant. It is generally known that that different *cannabis* strains produce different results and this is in part due to different terpene profiles. For example, even if 2 strains have the same cannabinoid content (THC, CBD, etc.), they often have different medical benefits and overall effects.

Terpenes are typically derived biosynthetically from units of isoprene, which has the molecular formula $C_5H_8$. The basic molecular formula of terpenes can be seen as multiples of that, $(C_5H_8)n$ where n is the number of linked isoprene units.

The at least one terpene of the present disclosure is preferably one or more of:
Alpha Bisabolol
Alpha Pinene
Beta Caryophyllene
Beta Pinene
Borneol
Camphene
Caryophyllene Oxide
Cineole
Delta 3 Carene
Eucalyptol
Fenchol
Fenchone
Geraniol
Guaiol
Humulene
Isopulegol
Limonene
Linalool
Myrcene
Nerol
Nerolidol
Ocimene
Phytol
Pulegone
Terpinene
Terpineol
Terpinolene and/or
Valencene The disclosure also encompasses pharmaceutical compositions comprising the at least one cannabinoid and/or the at least one terpene, or pharmaceutically acceptable salts or derivatives thereof in combination with psilocybin and/or psilocin, preferably formulated into pharmaceutical dosage forms, together with suitable pharmaceutically acceptable carriers, such as diluents, fillers, salts, buffers, stabilizers, solubilizers, etc. The dosage form may contain other pharmaceutically acceptable excipients for modifying conditions such as pH, osmolarity, taste, viscosity, sterility, lipophilicity, solubility etc. The choice of diluents, carriers or excipients will depend on the desired dosage form, which may in turn be dependent on the intended route of administration to a patient.

Suitable dosage forms include, but are not limited to, solid dosage forms, for example tablets, capsules, powders, dispersible granules, cachets and suppositories, including sustained release and delayed release formulations. Powders and tablets will generally comprise from about 5% to about 70% active ingredient. Solid carriers and excipients are generally known in the art and include, e.g. magnesium carbonate, magnesium stearate, talc, sugar, lactose, etc. Tablets, powders, cachets and capsules are all suitable dosage forms for oral administration.

Suitable liquid dosage forms include solutions, suspensions and emulsions. Liquid form preparations may be administered by intravenous, intracerebral, intraperitoneal, parenteral or intramuscular injection or infusion. Sterile injectable formulations may comprise a sterile solution or suspension of the active agent in a non-toxic, pharmaceutically acceptable diluent or solvent. Liquid dosage forms also include solutions or sprays for intranasal, buccal or sublingual administration. Aerosol preparations suitable for inhalation may include solutions and solids in powder form, which may be combined with a pharmaceutically acceptable carrier, such as an inert compressed gas.

Also encompassed are dosage forms for transdermal administration, including creams, lotions, aerosols and/or emulsions. These dosage forms may be included in transdermal patches of the matrix or reservoir type, which are generally known in the art.

Pharmaceutical preparations dose (for the cannabinoid, terpene and/or the psilocybin/psilocin) may be conveniently prepared in unit dosage form, according to standard procedures of pharmaceutical formulation.

The quantity of active compound(s) per unit dose may be varied according to the nature of the active compound and the intended dosage regime. Generally an effective amount shall be used, which may be within the range of from 0.01 mg to 5000 mg, preferably 0.01-4000 mg, 0.1-3000 mg, 1-2500, 5-1000, or 10-100 mg per unit dose (for the at least one cannabinoid and/or the at least one terpene and/or the at least one psilocybin and/or the at least one psilocin).

Generally, the weight ratio of the at least one cannabinoid and/or the at least one terpene to the at least one psilocybin/psilocin is decided by considering the properties of each constitute to be combined, the properties of drug combination and the symptoms of the patient. Preferably the weight ratio is in the range of 1 part by weight of the cannabinoid and/or terpene to about 0.01 to about 500 parts by weight of the psilocybin/psilocin, more preferably 1 part by weight of the cannabinoid/terpene to about 0.1 to about 100 parts by weight of the psilocybin/psilocin. More preferably the cannabinoid is a phyto-cannabinoid which may be present as a synthesized compound, an isolated compound or as an extract containing one or more other phyto-cannabinoids and other plant constituents in varying amounts. The extract may have had individual cannabinoids, such as THC, selectively removed in whole or part.

The present disclosure preferably aims for the prevention and/or treatment of autoimmune disorders such as Alzheimer's, Parkinson's, Huntington's, dementia, MS, ALS, etc. Also the prevention and/or treatment of depression is foreseen, as well as other mental illnesses.

The object of the present disclosure finds particular use in one or more of the following conditions:
Developmental disorders
Delirium, dementia, amnestic disorders and other cognitive disorders
Psychiatric disorders due to a somatic condition
Drug-related disorders
Schizophrenia and other psychotic disorders
Mood disorders
Anxiety disorders
Somatoform disorders
Factitious disorders
Dissociative disorders
Eating disorders
Sleep disorders
Impulse control disorders, not elsewhere classified
Adjustment disorders
Personality disorders Additionally or simultaneously, the object of the present disclosure finds use in one or more of the following conditions:
ADHD
ADD
Anorexia nervosa
Antisocial personality disorder Autism
Addiction
Avoidant personality disorder
Bipolar disorder
Bulimia Nervosa
Borderline personality disorder
Catatone schizophrenia
Chronic motor or vocal tic disorder
Conversion disorder
Cyclothymia
Dependent personality disorder
Delier
Dementia
Depersonalization disorder
Depression
Dhat syndrome
Dissociative amnesia
Dissociative fugue
Dissociative identity disorder
Dissociative disorder
Dissociative disorder, not otherwise specified
Dysthymic disorder
Da Costa's syndrome
Ephobophilia
Exhibitionism
Generalized anxiety disorder
Grandiose delusions
Hypochondria
Hoarding disorder
Intermittent explosive disorder
Jealousy
Kleptomania
Klüver-Bucy syndrome
Maternity psychosis
Mental retardation
Monomania
Münchhausen syndrome
Misophony
Narcissistic personality disorder
Obsessive-compulsive disorder
Oniomania
Organic personality disorder
Phobia
Paranoid personality disorder
Paranoid delusions
Passive-aggressive personality
Pathological gambling
Pathological lying
Personality disorder not otherwise defined (PDNOS)
Pervasive developmental disorder
Pica
Pain disorder
Post encephalitic syndrome
Postpartum depression
Posttraumatic stress disorder
Psychosis
Psychotic disorder due to substance use
Pyromania
Querulant delusions
Ruminational disorder
Schizophrenia
Schizoaffective disorder
Schizoid personality disorder
Schizotypal personality disorder
Separation anxiety
Social phobia
Somatisation disorder
Somatic delusion
Somatoform disorder
Syndrome of Capgras
Syndrome of Cotard
Syndrome of Ganser
Syndrome of Gilles de la Tourette
Selective mutism
Theatrical personality disorder
Trichotillomania
Undifferentiated somatoform disorder Example 1

In a 48-day treatment, 50 subjects suffering from diverse medical conditions receive a daily oral dose with either
pure psilocybin (30 mg);
pure cannabidiol (30 mg); or
combined treatment of pure psilocybin (30 mg)+pure cannabidiol (30 mg).

| No. of subjects | Diagnosed condition | Effect treatment with psilocybin | Effect treatment with cannabidiol | Effect combined treatment |
|---|---|---|---|---|
| 14 | Depression | 6 subjects report improved mood after period of treatment | 5 subjects report improved mood after period of treatment | 14 subjects report improved mood after period of treatment |
| 3 | Psychotic disorder | on average, 20% increased occurrence of psychotic episodes during period of treatment | on average, 10% increased occurrence of psychotic episodes during period of treatment | on average, 70% decreased occurrence of psychotic episodes during period of treatment |
| 2 | Schizophrenia | on average, 0% decreased occurrence of schizophrenic episodes during period of treatment | on average, 50% decreased occurrence of schizophrenic episodes during period of treatment | on average, 100% decreased occurrence of schizophrenic episodes during period of treatment |
| 4 | Anxiety disorder | on average, 50% increased occurrence of anxiety attacks during period of treatment | on average, 40% increased occurrence of anxiety attacks during period of treatment | on average, 50% decreased occurrence of anxiety attacks during period of treatment |
| 2 | Panic disorder | on average, 50% | on average, 40% | on average, 50% |

-continued

| No. of subjects | Diagnosed condition | Effect treatment with psilocybin | Effect treatment with cannabidiol | Effect combined treatment |
|---|---|---|---|---|
| 1 | Huntington's disease | Increased occurrence of panic attacks during period of treatment normal progression of movement, cognitive, and psychiatric disorders during treatment | Increased occurrence of panic attacks during period of treatment normal progression of movement, cognitive, and psychiatric disorders during treatment | decreased occurrence of panic attacks during period of treatment No progression of movement, cognitive, and psychiatric disorders during treatment |
| 10 | Alzheimer's disease | normal progression of disease symptoms during treatment | normal progression of disease symptoms during treatment | No progression of disease symptoms during treatment |
| 10 | Dementia | normal progression of disease symptoms during treatment | normal progression of disease symptoms during treatment | No progression of disease symptoms during treatment |
| 4 | Parkinson's disease | normal progression of movement disorders during treatment | normal progression of movement disorders during treatment | No progression of movement disorders during treatment |

Replacing cannabidiol with another cannabinoid may lead to similar results. Treatment according to the present disclosure leads to a decreased occurrence or decreased progression of symptoms in subjects suffering from depression, psychosis, schizophrenia, anxiety disorder, panic attacks, Huntington's disease, Alzheimer's disease, dementia, and/or Parkinson's disease. No side effects were observed.

Example 2

This example shows the beneficial role of terpenes. It is known that the use of different types of *cannabis* with similar characteristics (in terms of cannabinoids and their respective ratios) can have different effects among patients. For example, the use of various so-called Haze strains (which are all sativa dominant and have a THC content of 19-21%) showed that patients with different psychological complaints each chose their own favourite Haze strain. The effects in these patients were very similar After using their favourite *cannabis* strain they had no complaints and all patients could function normally. This makes it very likely that the terpenes, which vary enormously from strain to strain, are responsible for the desired effect of the cannabinoids. The same can be said about psilocybin and psilocin, that also have the potential to correct or enhance the effects of cannabinoids.

The invention claimed is:

1. A method for preventing or treating a psychological disorder in a patient, comprising:
   administrating psilocybin and/or psilocin in combination with at least one cannabinoid and/or at least one terpene, wherein the at least one cannabinoid and/or at least one terpene is administered separately, sequentially or simultaneously to the psilocybin and/or psilocin.

2. The method of claim 1, wherein the psychological disorder is chosen from depression, psychotic disorder, schizophrenia, schizophreniform disorder (acute schizophrenic episode); schizoaffective disorder; bipolar I disorder (mania, manic disorder, manic-depressive psychosis); bipolar II disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder, anxiety disorder, panic disorder, panic attacks, agoraphobia, attention deficit syndrome, premenstrual dysphoric disorder (PMDD), and premenstrual syndrome (PMS).

3. A method for preventing or treating a brain disorder in a patient, comprising:
   administrating psilocybin and/or psilocin in combination with at least one cannabinoid and/or at least one terpene, wherein the at least one cannabinoid and/or at least one terpene is administered separately, sequentially or simultaneously to the psilocybin and/or psilocin.

4. The method of claim 3, wherein the brain disorder is chosen from Huntington's disease, Alzheimer's disease, dementia, Parkinson's disease.

5. The method of claim 1, wherein the at least one cannabinoid is at least one, two or three chosen from the group consisting of cannabidiol (CBD); cannabidiolic acid (CBDA); tetrahydrocannbidivarin (THCV); tetrahydrocannbidivarinin acid (THCVA); cannabichromene (CBC); cannabichromenic acid (CBCA); cannabigerol (CBG) and cannabigerolic acid (CBGA).

6. The method of claim 1, wherein the at least one cannabinoid is present in the form of an extract from a *cannabis* plant.

7. The method of claim 1, wherein the at least one cannabinoid is present in a composition comprising at least 2, 3, or 4 cannabinoids.

8. The method of claim 1, wherein the at least one cannabinoid is present in a pure form.

9. The method of claim 1, wherein the at least one cannabinoid is present in a synthetic form.

10. The method of claim 1, wherein the psilocybin and/or psilocin are present in the form of an extract from a mushroom and/or truffle (*sclerotium*).

11. The method of claim 1, wherein the psilocybin and/or psilocin are present in a pure form.

12. The method of claim 1, wherein the psilocybin and/or psilocin are present in a synthetic form.

13. The method of claim 1, wherein psilocybin and/or psilocin in combination with the at least one cannabinoid and/or at least one terpene are comprised in a pharmaceutical composition.

14. A method for preventing or treating developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders in a patient, comprising:

administrating psilocybin and/or psilocin in combination with at least one cannabinoid and/or at least one terpene.

15. A method for preventing or treating of ADHD, ADD, anorexia nervosa, antisocial personality disorder, autism, addiction, avoidant personality disorder, bipolar disorder, bulimia nervosa, borderline personality disorder, catatone schizophrenia, chronic motor or vocal tic disorder, conversion disorder, cyclothymia, dependent personality disorder, delier, dementia, depersonalization disorder, depression, Dhat syndrome, dissociative amnesia, dissociative fugue, dissociative identity disorder, dissociative disorder, dissociative disorder, not otherwise specified, dysthymic disorder, Da Costa's syndrome, ephobophilia, exhibitionism, generalized anxiety disorder, grandiose delusions, hypochondria, hoarding disorder, intermittent explosive disorder, jealousy, kleptomania, Klüver-Bucy syndrome, maternity psychosis, mental retardation, monomania, Müchhausen syndrome, misophony, narcissistic personality disorder, obsessive-compulsive disorder, oniomania, organic personality disorder, phobia, paranoid personality disorder, paranoid delusions, passive-aggressive personality, pathological gambling, pathological lying, personality disorder not otherwise defined (PDNOS), pervasive developmental disorder, pica, pain disorder, post encephalitic syndrome, postpartum depression, posttraumatic stress disorder, psychosis, psychotic disorder due to substance use, pyromania, querulant delusions, ruminational disorder, schizophrenia, schizoaffective disorder, schizoid personality disorder, schizotypal personality disorder, separation anxiety, social phobia, somatisation disorder, somatic delusion, somatoform disorder, syndrome of Capgras, syndrome of Cotard, syndrome of Ganser, syndrome of Gilles de la Tourette, selective mutism, theatrical personality disorder, trichotillomania, or undifferentiated somatoform disorder in a patient, comprising:

administrating psilocybin and/or psilocin in combination with at least one cannabinoid and/or at least one terpene.

16. The method of claim 6, wherein the extract has all or a proportion of THC and/or THCA selectively removed.

17. The method of claim 10, wherein the mushroom is selected from the genus *Psilocybe, Gymnopilus, Panaeolus, Copelandia, Hypholoma, Pluteus, Inocybe, Conocybe, Panaeolina, Gerronema, Agrocybe, Galerina* and/or *Mycena*.

18. The method of claim 17, wherein the mushroom is selected from *P. azurescens, P. semilanceata, P. cyanescens*, and/or *P. cubensis, P. subcubensis, P. tampanensis, P. mexicana* A, *P. atlantis*, and/or *P. semilanceata*.

19. The method of claim 13, wherein psilocybin and/or psilocin in combination with the at least one cannabinoid and/or at least one terpene further comprises one or more pharmaceutically acceptable carriers, excipients or diluents.

* * * * *